United States Patent [19]
Dave et al.

[11] Patent Number: 5,708,017
[45] Date of Patent: Jan. 13, 1998

[54] STABLE, READY-TO-USE PHARMACEUTICAL PASTE COMPOSITION CONTAINING PROTON PUMP INHIBITORS

[75] Inventors: Kaushik J. Dave, Branchburg, N.J.; James B. Williams, Lansdale, Pa.

[73] Assignee: Merck & Co., Inc., Rahway, N.J.

[21] Appl. No.: 416,275

[22] Filed: Apr. 4, 1995

[51] Int. Cl.$^6$ .................................................. A61K 31/415
[52] U.S. Cl. ............................................ 514/393; 514/394
[58] Field of Search ..................................... 514/393, 394

[56] References Cited

U.S. PATENT DOCUMENTS

| | | | |
|---|---|---|---|
| 5,093,342 | 3/1992 | Tomoi et al. | 514/328 |
| 5,124,158 | 6/1992 | Ruwart et al. | 424/449 |
| 5,219,870 | 6/1993 | Kim | 514/338 |
| 5,554,631 | 9/1996 | Kim et al. | 514/338 |

FOREIGN PATENT DOCUMENTS

| | | |
|---|---|---|
| 0005129 | 10/1979 | European Pat. Off. . |
| 0166287 | 1/1986 | European Pat. Off. . |
| 0174726 | 3/1986 | European Pat. Off. . |
| 2163747 | 5/1986 | United Kingdom . |
| 94/25070 | 11/1994 | WIPO . |
| 9425070 | 11/1994 | WIPO . |

*Primary Examiner*—Kevin E. Weddington
*Attorney, Agent, or Firm*—Mollie M. Yang; David L. Rose

[57] ABSTRACT

The present invention is concerned with an oral pharmaceutical formulation containing a proton pump inhibitor (PPI) which is suitable for the treatment of gastric acid related diseases in man and animals. More specifically, the composition is a paste, and is particularly suitable for delivery of a proton pump inhibitor to horses.

8 Claims, No Drawings

STABLE, READY-TO-USE PHARMACEUTICAL PASTE COMPOSITION CONTAINING PROTON PUMP INHIBITORS

SUMMARY OF THE INVENTION

The present invention provides a stable oral pharmaceutical composition in a paste form containing a proton pump inhibitor as the active ingredient. The composition is useful for delivery of acid labile drugs to animals, particularly horses, and humans with difficulty in swallowing solid dosage forms such as tablets and capsules.

BACKGROUND OF THE INVENTION

Proton pump inhibitors (PPI) are potent inhibitors of gastric acid secretion by inhibiting $H^+K^+$-ATPase, the enzyme involved in the final step of hydrogen ion production in the parietal cells. Hence, PPI have been used in the treatment of gastric acid related diseases in humans. These diseases include gastric and duodenal ulcers. Peptic ulcers are common also in some animals, particularly in horses. Although the etiology of gastro-duodenal ulcers in horses has not been ascertained, it appears that stress plays an important roles in some cases.

PPIs are highly acid labile and hence oral formulations are enteric-coated. Enteric coated formulations are expensive and time consuming to manufacture, and requires elaborate technology and equipment. Another disadvantage of enteric coated formulation is its moisture sensitivity.

WO94/25070 discloses oral composition containing a proton pump inhibitor in the form of enteric coated dry particles mixed with a dry gelling agent, the mixture may then be made into a paste-like gel prior to administration. The composition therefore requires enteric coating, with the afore-mentioned disadvantages associated with such formulation. Furthermore, because such a moist gel is not stable during long-term storage at room temperature it cannot be manufactured and sold as a ready-to-use formulation, rather it must be prepared ex tempore at the time of administration, making it inconvenient to use.

The formulation described herein is a stable, ready to use semi-solid paste formulation containing a proton pump inhibitor suitable for administering to animals such as horses, cattle, pig etc, and human beings with difficulty swallowing solid dosage forms such as tablets and capsules. The present invention can be easily administered to horses and is readily accepted by these animals. The formulation of the present invention is stable during long-term storage at room temperature.

DETAILED DESCRIPTION OF THE INVENTION

The present invention provides a stable, ready-to-use oral pharmaceutical paste composition of PPI which can be readily administered to animals such as horses. More particularly, the present composition comprises: one or more proton pump inhibitors, a hydrophobic oily liquid vehicle, a basifying agent, and a thickening agent.

The proton pump inhibitors used in the present invention are compounds of the general formula

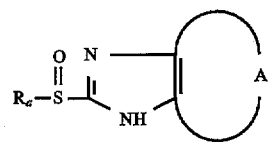

wherein $R_a$ is

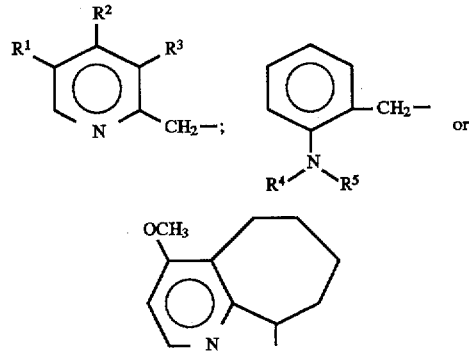

$R^1$ and $R^3$ are independently selected from hydrogen, lower alkyl, lower alkoxy and halogen, $R^2$ is selected from hydrogen, lower alkyl, lower alkoxy, lower alkoxy-lower alkoxy, lower fluoralkoxy and

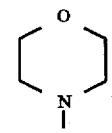

$R^4$ and $R^5$ are independently selected from lower alkyl, A is

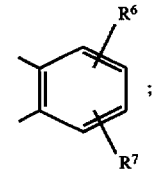

$R^6$ and $R^7$ are independently selected from hydrogen, lower alkyl, lower alkoxy, lower fluoroalkoxy, lower fluoroalkyl, halogen,

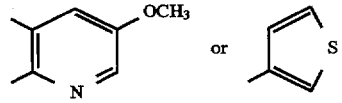

wherein $R^8$ is lower alkyl or lower alkoxy.

Examples of proton pump inhibitors according to Formula I are

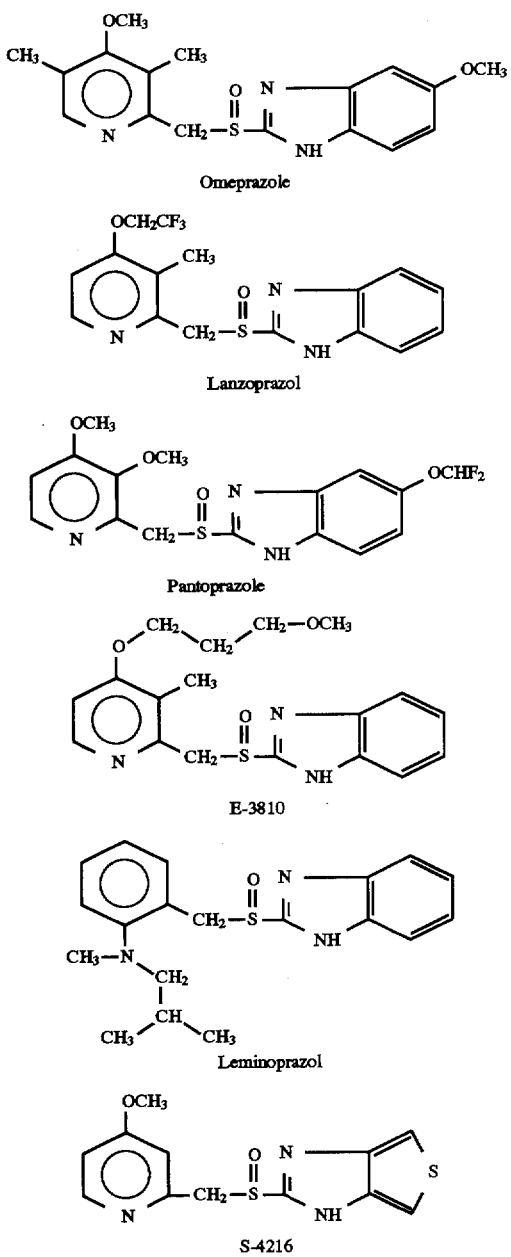

The preferred proton pump inhibitor used in the present invention is the compound known as omeprazole. The proton pump inhibitors used in the present invention are known compounds in the art, and methods for their preparation may be found in the literature. For example, omeprazole is disclosed in EP 5129, lansprazole in EP 174,726, pantoprazole in EP 166,287 and leminoprazole in GB 2,163, 747.

The hydrophobic oily liquid vehicle may be any pharmaceutically acceptable oil that are insoluble or practically insoluble in water; examples include mineral oil, almond oil, cottonseed oil, ethyl oleate, isopropyl myristate, isopropyl palmitate, myristyl alcohol, octyldodecanol, olive oil, penut oil, safflower oil sesame oil, soybean oil and squalene. The preferred hydrophobic oily liquid is one or more triglycerides of $C_6$–$C_{18}$ carboxylic acid; the preferred triglyceride is capric triglyceride or caprylic triglyceride, or a mixture thereof such as the product under the name Miglyol 810® (Huls America, Inc., New Jersey).

The thickening agent may be any pharmaceutically acceptable thickener that are insoluble or practically insoluble in water; examples include silicone dioxide, waxes such as castor wax or hydrogenated castor oil, paraffin, cetostearyl alcohol, and the like. The preferred hydrophobic thickener is hydrogenated castor oil.

Suitable basifying agents are for example pharmaceutically acceptable amine bases such as triethanolamine, or salts of carboxylic acids such as sodium acetate, sodium citrate, potassium sorbate, and the like. Preferred basifying agent is potassium sorbate.

The present compositon may include additional ingredients commonly used in the formulation of human and veterinary medicines. For example, flavoring agents such as caramel, carrot, apple, and sausage flavors; coloring agents such as iron oxide, titanium dioxide, aluminum lakes; sweeteners such as sugar, sodium saccharin; preservatives such as parabens; antioxidants such as BHT, BHA and viscosity regulating agents such as white wax or synthetic waxes such as glyceryl tribehenate, glyceryl trimyristate, hydrogenated coco-glycerides can be added.

The composition of the present invention may be prepared by dispersing the active ingredient, the proton pump inhibitor, in powder form in the hydrophobic liquid vehicle containing any other excipients except the thickening agent. The thickening agent is then added to the mixture and mixed to achieve the desired consistency. The paste formulation thus obtained may be used to fill dosing syringes, which may be used directly to adminster the active drug to an animal in need of treatment The amount of the proton pump inhibitor can vary from 1 to 35 percent w/w in the final composition, preferably from about 1 to about 25% w/w. The thickening agent comprises approximately 2 to 9 percent of the final composition; preferably, it is about 5 to 7% w/w. The hydrophobic vehicle is present as approximately 60 to 95 percent, depending on the amount of other excipients in the paste. The basifying agent is used in an amount sufficient to provide a non-acidic environment for the acid-labile proton pump inhibitors; typically, the amount of basifying agent is from about 0.01 to about 2% w/w, and 0.1% is usually sufficient.

The incorporation of acid labile drug substance in this formulation results in an orally palatable and pharmaceutically stable paste. The invention and the pharmacologically active ingredient remain stable.

The composition of the present invention are useful in the treatment of peptic ulcer diseases in humans or animals. It can be used to deliver acid labile drugs orally for systemic activity in animals. The composition can also be used for the delivery of the acid labile drugs in human with difficulty of swallowing solid dosage forms such as enteric coated tablets and capsules. The composition may be administered directly into the mouth of an animal, such as a horse, in need of anti-ulcer therapy; preferably a paste dosing syringe is used to facilitate drug administration. The consistency of this paste is such that it can not easily drip out or be expelled once it is deposited on the dorsal part of the animal's tongue. The paste is practically free of air bubbles which enhances dosing accuracy. Another advantage of this formulation is that individualized doses can be administered.

The amount of the composition to be administered may vary according to the particular animal species to be treated, the specific active ingredient in the composition, the severity of the disease, the physical condition of the afflicted animal, and other factors. A physician or veterinarian skilled in the art of ulcer treatment may read fly determined the proper dosage for the specific host under treatment. In general, a dose range of from about 0.2 mg/kg to about 20 mg/kg may be used.

EXAMPLE 1

| Omeprazole powder | 25.0 g |
| --- | --- |
| Capric/caprylic triglyceride | 67.9 g |
| Potassium sorbate | 0.1 g |
| Hydrogenated castor oil | 7.0 g |

Potassium sorbate (and, if present, additional excipients other than drag or thickener) is added to capric/caprylic triglyceride (Miglyol 810®) with mixing. Omeprazole powder is then added with mixing. Finally hydrogenated castor oil is added, and mixing continues for about 30 minutes/

EXAMPLE 2

| Omeprazole powder | 25.0 g |
| --- | --- |
| Capric/caprylic triglyceride | 67.8 g |
| Mapico yellow | 0.1 g |
| Potassium sorbate | 0.1 g |
| Hydrogenated castor oil | 7.0 g |

Following the procedure of Example 1, omeprazole paste of the above compositon is prepared.

EXAMPLE 3

| Omeprazole powder | 25.0 g |
| --- | --- |
| Capric/caprylic triglyceride | 67.8 g |
| Mapico red | 0.1 g |
| Potassium sorbate | 0.1 g |
| Hydrogenated castor oil | 7.0 g |

Following the procedure of Example 1, omeprazole paste of the above compositon is prepared.

EXAMPLE 4

| Omeprazole powder | 10.0 g |
| --- | --- |
| Capric/caprylic triglyceride | 84.0 g |
| Triethanolamine | 1.0 g |
| Silicon dioxide | 5.0 g |

Following the procedure of Example 1, omeprazole paste of the above compositon is prepared.

EXAMPLE 5

| Omeprazole powder | 22.0 g |
| --- | --- |
| Capric/caprylic triglyceride | 67.8 g |
| BHT | 0.01 g |
| Mapico Yellow | 0.1 g |
| Potassium sorbate | 0.1 g |
| Hydrogenated castor oil | 7.0 g |

Following the procedure of Example 1, omeprazole paste of the above compositon is prepared.

What is claimed is:

1. A stable, ready-to-use pharmaceutical paste composition for oral administration which comprises: a proton pump inhibitor, a thickening agent, a basifying agent, and a hydrophobic oily liquid vehicle.

2. A composition of claim 1 wherein said proton pump inhibitor is omeprazole.

3. A composition of claim 1 wherein said thickening agent is hydrogenated castor oil.

4. A composition of claim 1 wherein said hydrophobic liquid vehicle is capric/caprylic triglyceride.

5. A composition of claim 2 wherein said basifying agent is potassium sorbate.

6. A composition of claim 1 wherein said proton pump inhibitor is about 1 to about 35% by weight, and the thickening agent is about 2 to about 9% by weight.

7. A composition of claim 6 wherein said proton pump inhibitor is omeprazole, said thickening agent is hydrogenated castor oil, and the hydrophobic liquid vehicle is capric/caprylic triglyceride.

8. A composition of claim 1 wherein said proton pump inhibitor is omeprazole, said thickening agent is hydrogenated castor oil, said hydrophobic oil is capric/caprylic triglyceride, and said basifying agent is potassium sorbate.

* * * * *